(12) United States Patent
Mishima et al.

(10) Patent No.: US 6,685,687 B2
(45) Date of Patent: Feb. 3, 2004

(54) DISPOSABLE UNDERGARMENT FOR MANAGEMENT OF BODY WASTES

(75) Inventors: Yoshitaka Mishima, Kagawa-ken (JP); Takamitsu Igaue, Kagawa-ken (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 10/024,546

(22) Filed: Dec. 21, 2001

(65) Prior Publication Data

US 2002/0082570 A1 Jun. 27, 2002

(30) Foreign Application Priority Data

Dec. 25, 2000 (JP) .......................................... 2000-393722

(51) Int. Cl.[7] ............................................... A61F 13/15
(52) U.S. Cl. .................... 604/385.19; 604/355
(58) Field of Search ................... 604/327, 332–345, 604/355, 385.01, 385.14, 385.19

(56) References Cited

U.S. PATENT DOCUMENTS

| | | | |
|---|---|---|---|
| 4,368,733 A | * 1/1983 | Sanidas | 604/327 |
| 4,664,661 A | 5/1987 | Ferguson | |
| 4,784,656 A | * 11/1988 | Christian | 604/355 |
| 4,846,820 A | * 7/1989 | Jensen | 604/339 |
| 5,417,680 A | * 5/1995 | Kimura et al. | 604/385.28 |
| 6,114,597 A | * 9/2000 | Romare | 604/378 |
| 6,346,097 B1 | * 2/2002 | Blaney | 604/327 |
| 6,468,254 B2 | * 10/2002 | Gupton | 604/345 |
| 6,551,292 B1 | * 4/2003 | D'Acchioli et al. | 604/329 |
| 2002/0138058 A1 | * 9/2002 | Mishima et al. | 604/385.19 |

FOREIGN PATENT DOCUMENTS

| | | |
|---|---|---|
| DE | 0 966 933 | 12/1999 |
| WO | 99/00092 | 1/1999 |
| WO | WO 99 00092 | 1/1999 |

* cited by examiner

*Primary Examiner*—Weilun Lo
*Assistant Examiner*—Michael Bogart
(74) *Attorney, Agent, or Firm*—Lowe Hauptman Gilman & Berner LLP

(57) ABSTRACT

A disposable undergarment for management of body wastes includes a flat bag having an upper sheet provided with a hole and a guide means for body wastes formed around the hole. The guide means includes an elastically stretchable and flexible guide tube and a flange formed around an upper opening of the guide tube. The flange is applied on its upper surface with pressure-sensitive adhesive.

22 Claims, 4 Drawing Sheets

US 6,685,687 B2

DISPOSABLE UNDERGARMENT FOR MANAGEMENT OF BODY WASTES

BACKGROUND OF THE INVENTION

This invention relates to a disposable undergarment for fecal management adapted to be suitable for management of feces, particularly of loose feces.

Bulletin No. WO 99/00092 discloses an undergarment for fecal management in the form of a bag. This bag has an opening and a flange surrounding the opening wherein the flange is coated on its upper surface with pressure-sensitive adhesive. This bag is adapted to be used in combination with a disposable diaper. To wear such combination, the bag is positioned on an inner side of the disposable diaper and the flange is adhesively fastened to a wearer's body around the anus.

However, with the known bag, the movement of the wearer's body relative to the disposable diaper is transmitted to the bag and may tend to peel the flange off from the wearer's body around the anus. To overcome this anxiety, an adhesive force of the pressure-sensitive adhesive coating the flange may be enhanced. From the other viewpoint, a weight of loose feces received in the bag may partially space the bag apart from the diaper and consequently the bag may hang down from the wearer's body around the anus. Such a likelihood also can be avoided by sufficiently enhancing the adhesive force of the pressure-sensitive adhesive to resist the increased weight of the bag. However, the adhesive force exerted on the flange would result in that the wearer suffers from pain when the wearer tends to peel the flange off from the wearer's skin and the wearer's skin is liable to suffer from eruption due to the pressure-sensitive adhesive.

SUMMARY OF THE INVENTION

It is an object of this invention to improve the disposable undergarment provided with the bag for management of body wastes such as loose feces so that the bag can be fastened to the wearer's skin without need for excessively high adhesive force.

According to this invention, there is provided a disposable undergarment for management of body wastes comprising a flat bag having an upper sheet and a lower sheet, a guide means formed on the upper sheet so as to guide body wastes into the bag and pressure-sensitive adhesive fastener means provided on the guide means to detachably fasten the guide means to the wearer's skin.

The guide means extend upward from a periphery of a hole formed in the upper sheet and comprise a tubular portion which is elastically stretchable in a vertical direction and flexible and a flange formed around an upper opening of the tubular portion wherein the fastener means comprise adhesive applied on upper the surface of the flange.

DETAILED DESCRIPTION OF THE PREFERRED EMBODIMENTS

Details of a disposable undergarment for management of body wastes according to this invention will be more fully understood from the description of a loose feces managing bag as one embodiment of this invention given hereunder with reference to the accompanying drawings.

Figure 1:
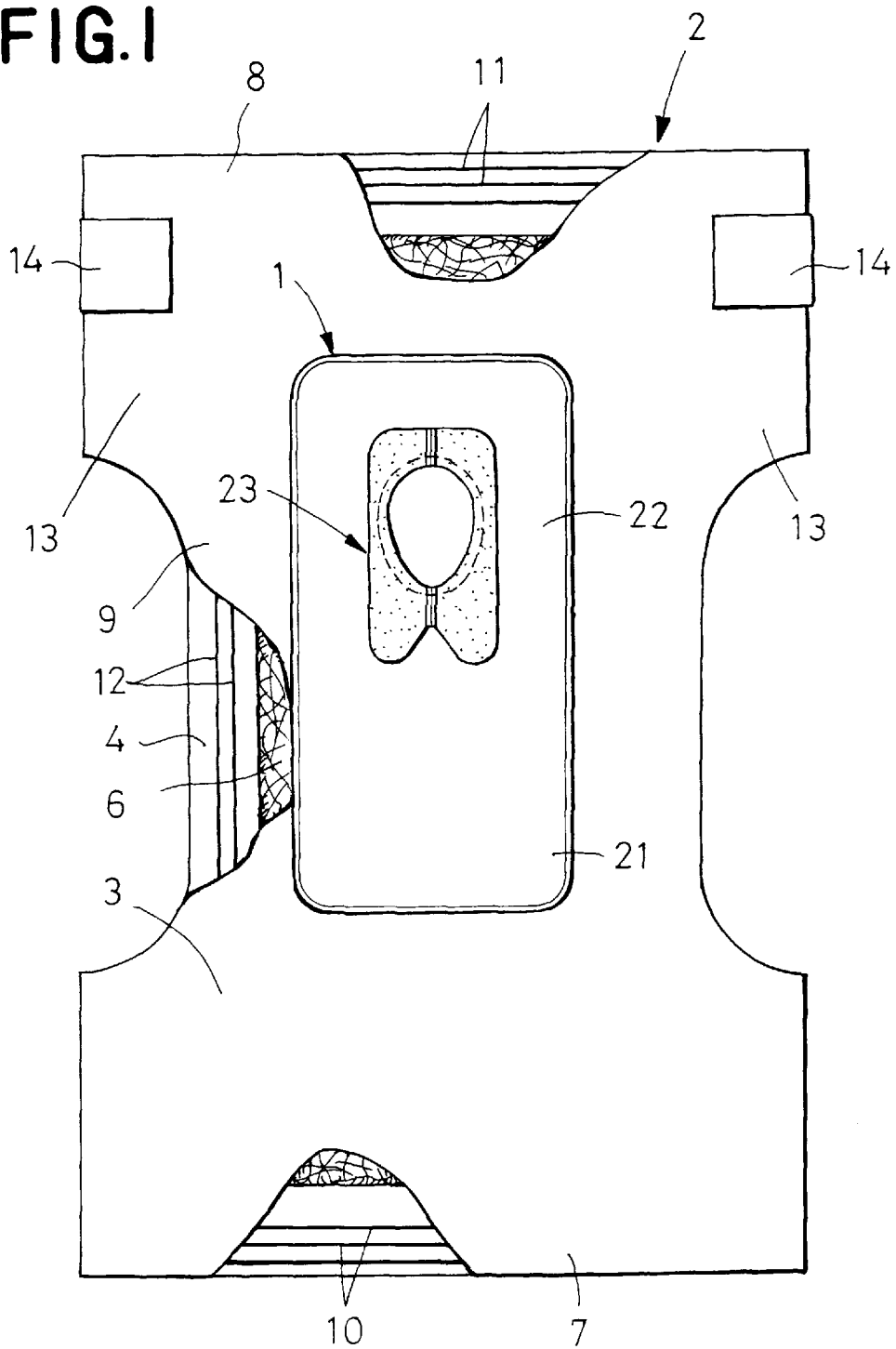
FIG. 1 is a plan view of an undergarment for management of body wastes placed on a disposable diaper.

FIG. 1 is a partially cutaway plan view of a bag 1 for management of loose feces placed on an inner side of a disposable diaper 2 adapted to be used with the bag 1. The diaper 2 is of well known art comprising a liquid-pervious topsheet 3, a liquid-impervious backsheet 4 and a liquid-absorbent core 6 disposed between these two sheets 3, 4. The diaper 2 is provided along longitudinally opposite end portions 7, 8 extending in a waist surrounding direction and transversely opposite side edge portions 9 each extending in a thigh surrounding direction with elastic members 10, 11 operatively associated with a waist-opening and elastic members 12 operatively associated with leg-opening. These elastic members 10, 11, 12 are disposed between the top- and backsheets 3, 4 and joined under extension to an inner surface of at least one of these top- and backsheets 3, 4 so as to extending in the respective surrounding directions. The diaper 2 has a pair of tape fasteners 14 attached to transversely opposite side edge portions 13 of its rear waist region, respectively.

The bag 1 presents a rectangular shape which is relatively long in a longitudinal direction (i.e., in a vertical direction as viewed in FIG. 1) of the diaper 2 and has a front region 21 and a rear region 22. The bag 1 is formed in a transversely middle zone of the rear region 22 with a guide means 23 for loose feces. The bag 1 is worn in combination with the diaper 2 in a manner that the front region 21 is oriented forwardly of the diaper 2 with the guide means 23 for loose feces fastened to the wearer's body around the anus.

Figure 2:
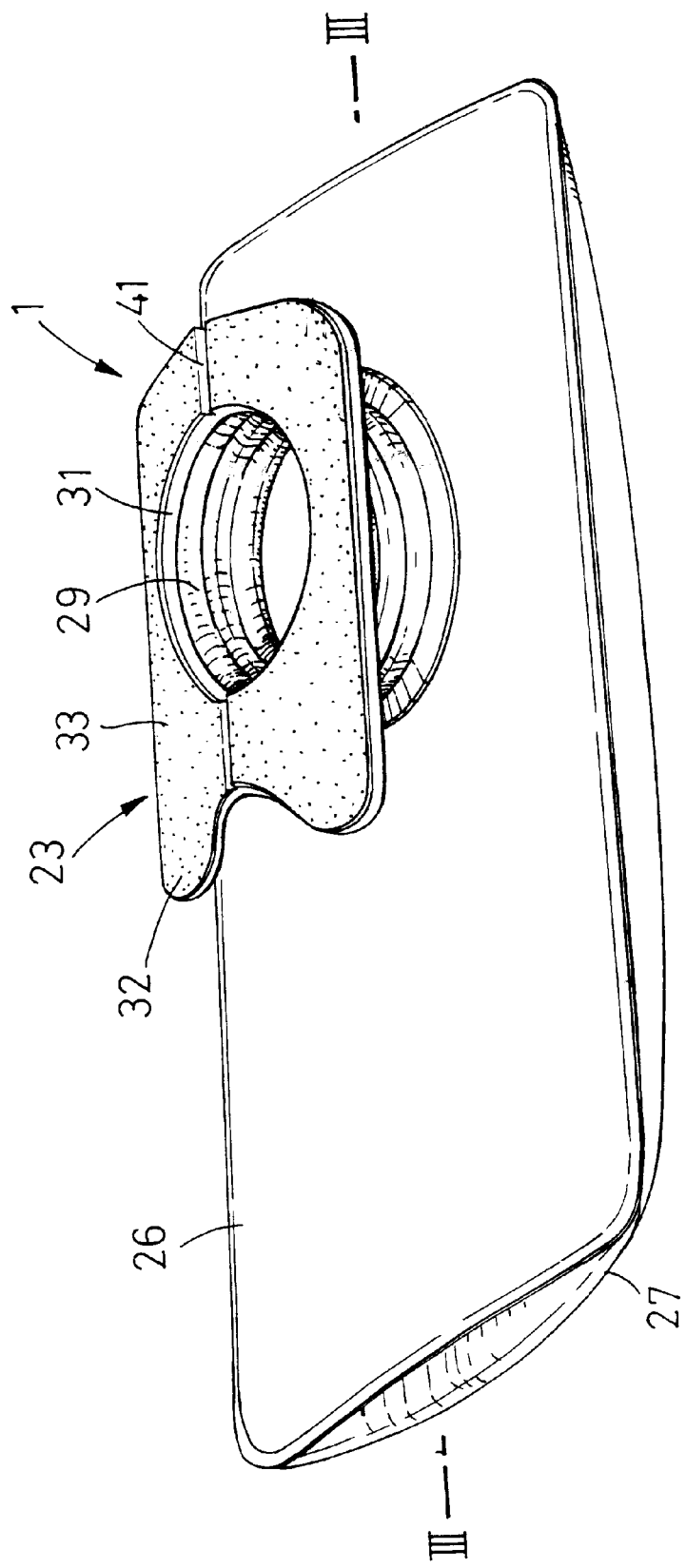
FIG. 2 is a partially cutaway perspective view of the undergarment for management of body wastes.
Figure 3:
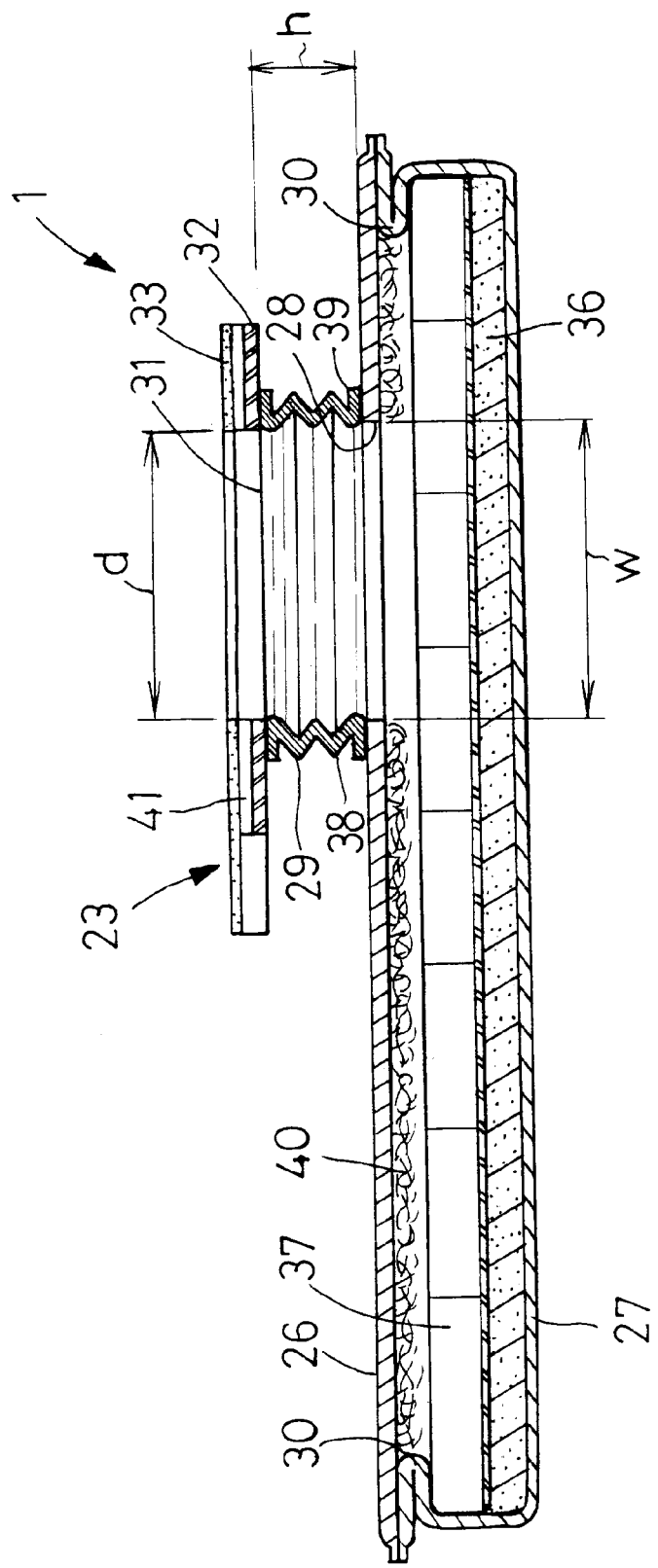
FIG. 3 is a sectional view taken along a line III—III.

FIG. 2 is a perspective view of the bag 1 and FIG. 3 is a sectional view taken along a line III—III in FIG. 2. The bag 1 is formed by placing upper and lower sheets 26, 27 both being rectangular upon and adhesively joined or welded to each along peripheral edges of these sheets 26, 27. The upper sheet 26 is formed with a hole 28 communicating with both the interior and the exterior of the bag 1 while the lower sheet 27 is formed along longitudinally opposite end portions of the bag 1 with reinforcing pleats 30, respectively. The guide means 23 include a guide tube 29 adapted to guide a flow of loose feces into the bag 1 and this guide tube 29 extend upward from a peripheral zone around the hole 28 substantially at right angles to the upper sheet 26. The guide tube 29 has an upper opening 31 around which a flange 32 is formed. The flange 32 is entirely or intermittently applied on its upper surface with pressure-sensitive adhesive 33.

The upper sheet 26 is made of a liquid-pervious nonwoven fabric, a liquid-pervious perforated plastic film or a liquid-impervious plastic film. The lower sheet 27 is made of a liquid-impervious plastic film, more preferably of breathable and a liquid-impervious plastic film. A liquid-absorbent layer 36 made of a water-absorbent material such as fluff pulp and/or super-absorptive polymer particles is disposed between the upper and lower sheets 26, 27. Preferably, a body fluid distribution layer 37 formed by a soft and elastic material such as foamed polyurethane, foamed polyethylene or foamed polystyrene overlies on the liquid-absorbent layer 36.

The guide tube 29 is elastically stretchable in the vertical direction as viewed in FIG. 3 and tiltable at an angle of 45° or more in its radial direction toward the upper sheet 26. To facilitate this, the guide tube 29 made of a liquid-impervious elastic material such as urethane or silicone rubber is provided in the form of bellows having undulations 38. It is also possible to form the guide tube 29 by providing a coil spring adapted to be elastically stretchable and adhesively covering the outer periphery of this coil spring with a substantially liquid-impervious nonwoven fabric or a liquid-impervious plastic film or the like having a water pressure resistance of 50 mm/H²O. The guide tube 29 has its proximal end portion 39 water-tightly joined to the upper sheet 26. The flange 32 lying on the top of the guide tube 29 is formed by a flexible and elastic sheet, for example, a foamed polyethylene sheet or a foamed polyurethane sheet. The flange 32 is formed on its upper or lower surface with a groove 41 extending in the longitudinal direction so as to bisect a width of the flange 32. This groove 41 facilitates the flange 32 to be folded upward and downward around this groove 41 and thereby to be placed closely against the wearer's skin around the anus.

Figure 4:
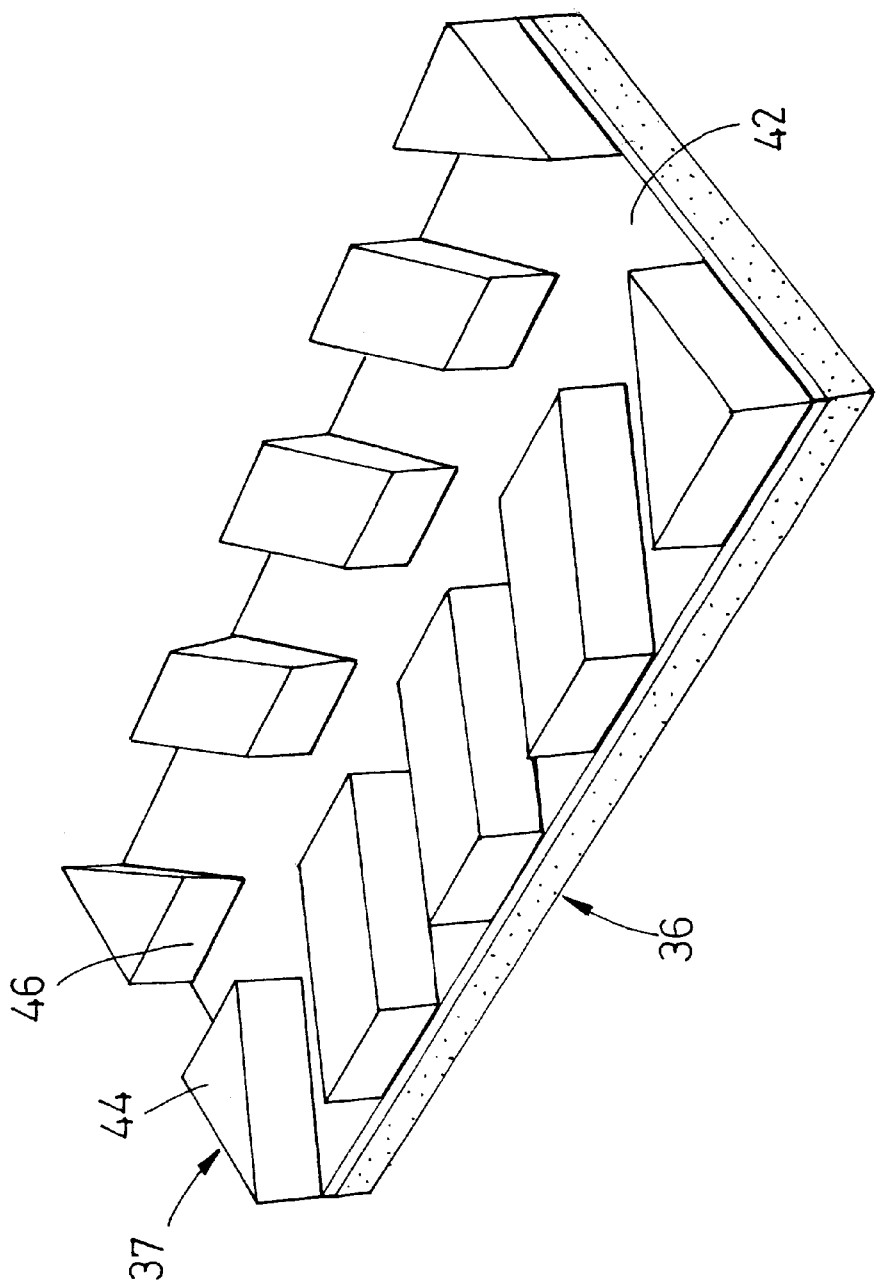
FIG. 4 is a partially cutaway perspective view of a liquid-absorbent layer and a body fluid distribution layer.

FIG. 4 is a perspective view showing an assembly of the liquid-absorbent layer 36 and the body fluid distribution layer 37. The liquid-absorbent layer comprises fluff pulp or a mixture of fluff pulp and super-absorptive polymer particles compressed together in the form of a panel. The body fluid distribution layer 37 comprises a plurality of blocks 44 made of materials such as foamed polyurethane each having a three-dimensional network structure and placed on the upper side of the panel-like liquid-absorbent layer 36 with a water-absorbent sheet 42 such as tissue paper or a net-like water-absorbent sheet lying there between. Each pair of the adjacent blocks 44 define therebetween a groove 46 adapted to distribute the body wastes such as loose feces introduced through the guide tube 29 into respective regions of the bag 1. A height of the blocks 44 may be appropriately adjusted while the upper and lower sheets 26, 27 may be spaced apart from each other by an appropriate dimension to facilitate loose feces to flow into the bag 1. The respective blocks 44 are joined to the water-absorbent sheet 42 and thereby maintained in predetermined relative positions.

The loose feces guide means 23 of the bag 1 is preferably dimensioned so that a diameter d of the guide tube 29 measured at the upper opening 31 and a height h of the guide tube 29 are in relationship of $d \geq h$ while this diameter d and a diameter w of the aperture 28 of the upper sheet 26 are in relationship of $d \geq w$. With the loose feces guide means 23 dimensioned in this manner, the upper opening 31 can not be readily closed even if the guide tube 29 tilts at a relatively large angle toward the upper sheet 26.

When the combination of the bag 1 and the diaper 2 is worn with the flange 32 of the bag 1 fastened to the wearer's body around the anus, the bag 1 is supported upward by the diaper 1, so no force tending to peel the flange 32 off from the wearer's skin is exerted on the flange 32. Shift of the bag 1 together with the diaper 2 relative to the wearer's body deforms the guide tube 29 so as to follow such shift so that a force exerted on the flange 32 and tending to peel the flange 32 off from the wearer's skin may be effectively alleviated. Even if the diaper 2 slips down along the wearer's waist and more or less spaced apart from the bag 1, the guide tube 29 is stretched downward under a weight of the bag 1 until the bag 1 comes in contact with the diaper 2. As a result, the bag 1 is maintained to be supported upward by the diaper 2 and a force exerted on the flange 32 due to the weight of the bag 1 can be alleviated. In this bag 1, the elastically stretchable guide tube 29 advantageously enables the flange 32 to be coated with pressure-sensitive adhesive 33 having a moderate adhesive force instead of an excessively high adhesive force. Therefore, the flange 32 applied with pressure-sensitive adhesive having such moderate adhesive force rarely causes the wearer not only to suffer from a pain when the flange 32 is peeled off from his or her skin but also to suffer from skin eruption.

In the embodiment according to which the upper sheet 26 of the bag 1 is liquid-pervious, discharged urine can be received by the front region 21 of the bag 1 and then guided to permeate the upper sheet 26 to the inner side of the bag 1. To facilitate this permeation, a perforated plastic film, if this is used as the upper sheet 26, this film is preferably provided on its inner surface with liner made of a hydrophilic fibrous assembly having a basis weight of 20–50 g/m². If a liquid-pervious nonwoven fabric is used as the upper sheet 26, this nonwoven fabric is provided on its inner surface with a liner made of hydrophilic fibrous assembly (See FIG. 3) having a density higher than that of the nonwoven fabric. If it is not required to manage urine, this invention may be implemented using the liquid-impervious upper sheet 26.

The lower sheet 27 of the bag 1 may be applied on a part of its outer surface with pressure-sensitive adhesive of provided with male members of a mechanical fastener commonly known as the trade mark "VELCRO" to detachably fasten the lower sheet 27 to the topsheet 3 of the diaper 2.

While the bag 1 has been illustrated and described to be used with the disposable diaper 2, the bag 1 may be used in combination with diaper cover or pants.

In the disposable undergarment for management of body wastes according to this invention, the flat bag is provided with the elastically stretchable and flexible guide tube for body wastes and this guide tube is provided around its top opening with the pressure-sensitive adhesive applied flange. With such a unique arrangement, shift of the bag relative to the wearer's body deforms the guide tube so as to follow such shift so that a force exerted on the flange and tending to peel the flange off from the wearer's skin is effectively alleviated. consequently, this undergarment for management of body wastes enables the flange to be coated with pressure-sensitive adhesive and thereby alleviates not only a pain possibly suffered from by the wearer when the flange is peeled off from wearer's skin but also an anxiety of skin eruption possibly suffered from by the wearer due to pressure-sensitive adhesive.

What is claimed is:

1. A disposable undergarment for management of body wastes, said undergarment comprising:
   a flat bag including an upper sheet having a hole formed therein, and a lower sheet;
   a guiding element formed on said upper sheet for guiding body wastes of a wearer into said bag, said guiding element comprising
      a flexible, tubular portion which extends in an upward direction from a periphery of the hole formed in said upper sheet, and is elastically stretchable in said upward direction, and
      a flange formed around an upper opening of said tubular portion; and
   a pressure-sensitive adhesive provided on an upper surface of said flange for detachable attachment of the guiding element to the wearer's skin;
   wherein, said upper sheet is liquid-pervious and said lower sheet is liquid-impervious.

2. A disposable undergarment for management of body wastes, said undergarment comprising:
   a flat bag including an upper sheet having a hole formed therein, and a lower sheet;
   a guiding element formed on said upper sheet for guiding body wastes of a wearer into said bag, said guiding element comprising a flexible, tubular portion which extends in an upward direction from a periphery of the hole formed in said upper sheet, and is elastically stretchable in said upward direction, and a flange formed around an upper opening of said tubular portion; and a first pressure-sensitive adhesive provided on an upper surface of said flange for detachable attachment of the guiding element to the wearer's skin;

wherein said bag is provided on a lower surface of said lower sheet with a second pressure-sensitive adhesive or a mechanical fastener.

3. The undergarment according to claim 1, wherein said bag further includes therein a liquid-absorbent layer and a distribution layer both for said body wastes.

4. The undergarment according to claim 1, wherein the hole of said upper sheet has an opening area that is larger than or equal to an area of the upper opening of said tubular portion.

5. The undergarment according to claim 1, wherein the upper opening of said tubular portion has a diameter that is larger than or equal to a length of said tubular portion.

6. The undergarment according to claim 1, wherein said tubular portion is tiltable at an angle of at least 45° relative to said upward direction.

7. The undergarment according to claim 2, wherein said bag further includes therein a liquid-absorbent layer and a distribution layer both for said body wastes.

8. The undergarment according to claim 2, wherein the hole of said upper sheet has an opening area that is larger than or equal to an area of the upper opening of said tubular portion.

9. The undergarment according to claim 2, wherein the upper opening of said tubular portion has a diameter that is larger than or equal to a length of said tubular portion.

10. The undergarment according to claim 2, wherein said tubular portion is tiltable at an angle of at least 45° relative to said upward direction.

11. The undergarment according to claim 2, further comprising a diaper having a topsheet attached to the lower sheet of said bag by said second pressure-sensitive adhesive or mechanical fastener.

12. A disposable human waste management bag, comprising a wearer facing sheet and a garment facing sheet opposed thereto, the wearer facing sheet having an aperture and being liquid-pervious, the garment facing sheet being liquid-impervious;

a tubular conduit extending from the aperture of the wearer facing sheet in a direction away from the garment facing sheet; and an adhesive coated flange provided on top of said tubular conduit for detachable attachment of the bag to a wearer's skin.

13. The bag according to claim 12, further comprising a liquid-absorbent layer between said wearer facing sheet and garment facing sheet.

14. The bag according to claim 12, wherein the aperture of said wearer facing sheet has an opening area that is larger than or equal to an area of an opposite opening of said tubular conduit, said opposite opening being surrounded by said flange.

15. The bag according to claim 14, wherein the opposite opening of said tubular conduit has a diameter that is larger than or equal to a length of said tubular conduit.

16. The bag according to claim 12, wherein said tubular conduit is elastically stretchable in said direction and tiltable at an angle of at least 45° relative to said direction.

17. A disposable human waste management bag, comprising a wearer facing surface and a garment facing surface opposed thereto, the wearer facing surface having an aperture;

a tubular conduit extending from the aperture of the wearer facing surface in a direction away from the garment facing surface;

an adhesive coated flange provided on top of said tubular conduit for detachable attachment of the bag to a wearer's skin; and a fastener provided on the garment facing surface and adapted to attach the bag to a cover garment.

18. The bag according to claim 17, wherein said fastener comprises one of a pressure-sensitive adhesive and a mechanical fastener.

19. The bag according to claim 17, further comprising therein a liquid-absorbent layer.

20. The bag according to claim 17, wherein the aperture of said wearer facing surface has an opening area that is larger than or equal to an area of an opposite opening of said tubular conduit, said opposite opening being surrounded by said flange.

21. The bag according to claim 20, wherein the opposite opening of said tubular conduit has a diameter that is larger than or equal to a length of said tubular conduit.

22. The bag according to claim 17, wherein said tubular conduit is elastically stretchable in said direction and tiltable at an angle of at least 45° relative to said direction.

* * * * *